US008021277B2

(12) United States Patent  (10) Patent No.: US 8,021,277 B2
Baudhuin  (45) Date of Patent: Sep. 20, 2011

(54) PROGRAMMED EXERCISE BICYCLE WITH COMPUTER AIDED GUIDANCE

(75) Inventor: John Baudhuin, Venice, CA (US)

(73) Assignee: Mad Dogg Athletics, Inc., Venice, CA (US)

( * ) Notice: Subject to any disclaimer, the term of this patent is extended or adjusted under 35 U.S.C. 154(b) by 1162 days.

(21) Appl. No.: 11/050,460

(22) Filed: Feb. 2, 2005

(65) Prior Publication Data

US 2006/0189439 A1 Aug. 24, 2006

(51) Int. Cl.
*A63B 71/00* (2006.01)
(52) U.S. Cl. .............................. 482/57; 482/8; 482/901
(58) Field of Classification Search .................. 482/1–9, 482/900–902, 51, 57; 434/247
See application file for complete search history.

(56) References Cited

U.S. PATENT DOCUMENTS

| 562,198 | A | 6/1896 | Robinson |
| 588,166 | A | 8/1897 | McCoy |
| 633,534 | A | 9/1899 | Read |
| 635,082 | A | 10/1899 | Stiles |
| 671,785 | A | 4/1901 | Young et al. |
| 1,336,774 | A | 4/1920 | Cooper |
| 1,507,554 | A | 9/1924 | Cooper |
| 1,636,327 | A | 7/1927 | Roe |
| 3,062,204 | A | 11/1962 | Stefano |
| 3,511,097 | A | 5/1970 | Corwin |
| D251,747 | S | 5/1979 | Valentine et al. |
| 4,188,030 | A | 2/1980 | Hooper |
| 4,298,893 | A | 11/1981 | Holmes |
| 4,408,613 | A | 10/1983 | Relyea |
| 4,512,566 | A | 4/1985 | Bicocchi |
| 4,512,567 | A | 4/1985 | Phillips |
| D280,117 | S | 8/1985 | Collins |
| D280,118 | S | 8/1985 | Collins |
| 4,577,860 | A | 3/1986 | Matias |
| D284,596 | S | 7/1986 | McNeil |
| 4,632,386 | A | 12/1986 | Beech |
| D289,782 | S | 5/1987 | Szymski et al. |
| 4,674,741 | A | 6/1987 | Pasierb, Jr. et al. |
| D291,462 | S | 8/1987 | Aalto |
| D292,304 | S | 10/1987 | Ostrom |
| 4,709,917 | A | 12/1987 | Yang |
| 4,711,447 | A | 12/1987 | Mansfield |
| 4,768,777 | A | 9/1988 | Yang |

(Continued)

FOREIGN PATENT DOCUMENTS

EP 0214748 3/1987

(Continued)

OTHER PUBLICATIONS

PCT International Search Report dated Jul. 14, 1995, International Application No. PCT US/95/03878.

(Continued)

*Primary Examiner* — Glenn Richman
(74) *Attorney, Agent, or Firm* — Maceiko IP

(57) ABSTRACT

The invention pertains to a stationary exercise bike along with a display that provides instruction to lead a rider through an exercise program. The invention allows a rider to obtain benefits of a group, instructor-led class though the rider's schedule does not permit the rider to participate in the class. The invention also describes a method of exercising with the foregoing bike and display.

30 Claims, 4 Drawing Sheets

U.S. PATENT DOCUMENTS

| | | | |
|---|---|---|---|
| 4,772,069 A | | 9/1988 | Szymski |
| 4,824,102 A | | 4/1989 | Lo |
| 4,867,442 A | | 9/1989 | Matthews |
| 4,880,225 A | | 11/1989 | Lucas et al. |
| 4,902,001 A | | 2/1990 | Balbo |
| 4,915,374 A | | 4/1990 | Watkins |
| 4,919,418 A | | 4/1990 | Miller |
| 4,936,570 A | | 6/1990 | Szymski et al. |
| 5,000,469 A | | 3/1991 | Smith |
| 5,001,632 A | | 3/1991 | Hall-Tipping |
| 5,067,710 A | | 11/1991 | Watterson et al. |
| 5,145,477 A | | 9/1992 | Han |
| 5,149,084 A | | 9/1992 | Dalebout et al. |
| 5,207,621 A | | 5/1993 | Koch et al. |
| 5,232,422 A | | 8/1993 | Bishop, Jr. |
| 5,308,296 A | | 5/1994 | Eckstein |
| 5,335,188 A | * | 8/1994 | Brisson .................. 702/163 |
| 5,336,147 A | | 8/1994 | Sweeney, III |
| 5,362,069 A | | 11/1994 | Hall-Tipping |
| 5,383,826 A | * | 1/1995 | Michael .................. 482/3 |
| 5,423,728 A | | 6/1995 | Goldberg |
| 5,489,249 A | | 2/1996 | Brewer et al. |
| 5,512,025 A | | 4/1996 | Dalebout et al. |
| 5,584,700 A | | 12/1996 | Feldman et al. |
| 5,643,146 A | * | 7/1997 | Stark et al. ............ 482/63 |
| 5,645,513 A | | 7/1997 | Haydocy et al. |
| 5,667,459 A | | 9/1997 | Su |
| 5,702,323 A | | 12/1997 | Poulton |
| 5,782,639 A | | 7/1998 | Beal |
| 5,785,631 A | | 7/1998 | Heidecke |
| 5,810,696 A | | 9/1998 | Webb |
| 5,830,107 A | | 11/1998 | Brigliadoro |
| 5,836,770 A | | 11/1998 | Powers |
| 5,888,172 A | | 3/1999 | Andrus et al. |
| 5,890,995 A | | 4/1999 | Bobick et al. |
| 5,916,063 A | | 6/1999 | Alessandri |
| 5,947,868 A | | 9/1999 | Dugan |
| 6,004,243 A | | 12/1999 | Ewert |
| 6,027,428 A | | 2/2000 | Thomas et al. |
| 6,059,692 A | | 5/2000 | Hickman |
| 6,152,856 A | | 11/2000 | Studor et al. |
| 6,287,239 B1 | | 9/2001 | Hernandez |
| 6,447,424 B1 | | 9/2002 | Ashby et al. |
| 6,450,922 B1 | | 9/2002 | Henderson et al. |
| 6,522,255 B1 | * | 2/2003 | Hsieh .................. 340/657 |
| 6,547,702 B1 | | 4/2003 | Heidecke |
| 6,626,799 B2 | | 9/2003 | Watterson et al. |
| 6,672,991 B2 | | 1/2004 | O'Malley |
| 6,793,608 B2 | | 9/2004 | Goldberg |
| 6,881,176 B2 | | 4/2005 | Oishi et al. |
| 6,932,745 B1 | | 8/2005 | Ellis |
| 7,022,048 B1 | * | 4/2006 | Fernandez et al. .......... 482/8 |
| 7,044,891 B1 | | 5/2006 | Rivera |
| 7,097,588 B2 | * | 8/2006 | Watterson et al. .......... 482/8 |
| 7,166,064 B2 | | 1/2007 | Watterson et al. |
| 7,179,202 B2 | | 2/2007 | Marin et al. |
| 7,435,202 B2 | * | 10/2008 | Daly et al. .................. 482/52 |
| 7,455,622 B2 | | 11/2008 | Watterson et al. |
| 7,481,744 B2 | | 1/2009 | Reyes et al. |
| 7,510,509 B2 | | 3/2009 | Hickman |
| 2004/0014566 A1 | * | 1/2004 | Kao .................. 482/8 |
| 2005/0075213 A1 | | 4/2005 | Arick |
| 2006/0046905 A1 | | 3/2006 | Doody, Jr. et al. |
| 2007/0170688 A1 | | 7/2007 | Watson |
| 2007/0197345 A1 | | 8/2007 | Wallace et al. |
| 2007/0219059 A1 | | 9/2007 | Schwartz et al. |
| 2008/0141135 A1 | | 6/2008 | Mason et al. |

FOREIGN PATENT DOCUMENTS

| | | |
|---|---|---|
| WO | WO9636399 A1 | 11/1996 |
| WO | WO9815112 A3 | 4/1998 |
| WO | WO9900782 A1 | 7/1999 |

OTHER PUBLICATIONS

Sheldon Brown's Bicycle Glossary; www.sheldonbrown.com/glossary.html.

Cateye GameBike Bicycle Indoor Trainer Accessory; http://www.lifestylesport.com/cateye_gamebike.htm.

Cateye CS 1000 CycloSimulator;http://www.lifestylesport.com/cs1000.htm.

Kurt Kinetic Trainers; http://www.lifestylesport.com/kurt_kinetic_trainers.htm.

Life Cycle Entertainment; http://www.fitego.com/lifcycexrem.html.

LCD Technology Life Fitness; http://us.commercial.lifefitness.com/content.cfm/lcd.

Life Fitness Lifecycle 9500 HRT Remanufactured; http://www.egymequipment.com/egymequipment-store/lif95hrtupre.html.

Exercise Bike LifeCycle 9100 Upright (Remanufactured); http://www.bigfitness.com/bigfit/liffitbrlif9.html.

Lee W. Young, Written Opinion of the International Searching Authority for PCT/US 09/01327, Apr. 27, 2009.

Spinning Phase I Learning With Johnny G., VHS Video Tape, 1996, PPI Entertainment Group, a division of Peter Pan Industries, Inc., 88 Francis St. Newark, NJ 07105.

Spinning Phase II Riding With Johnny G., VHS Video Tape, 1996, PPI Entertainment Group, a division of Peter Pan Industries Inc., 88 Francis St. Newark, NJ 07105.

* cited by examiner

PROGRAMMED EXERCISE BICYCLE WITH COMPUTER AIDED GUIDANCE

FIELD OF THE INVENTION

The invention generally relates to exercise devices and programs. More specifically, the invention relates to providing instructions to an exercise participant to lead the participant through an exercise program. The invention also relates to the use of a stationary exercise bike on which the participant may exercise.

An embodiment of the invention relates to the use of an indoor exercise bike along with instructions similar to those provided by an instructor during a indoor exercise bike program. In this embodiment, the participant is instructed to assume different hand and riding positions throughout the program.

BACKGROUND OF THE INVENTION

In recent years, instructor-led exercise classes using stationary exercise bikes have become increasingly popular. Since the advent of the indoor cycling exercise program, various indoor cycling classes have come into existence. In such classes, the instructor typically leads a class of participants by instructing them to assume different riding positions, such as sitting and standing in combination with different hand positions on the handlebars. The instructor also may instruct participants to vary their pedaling cadence to simulate sprinting or other riding conditions. The bikes used in these classes typically have a resistance device to vary how difficult it is to pedal, and the instructor may also instruct participants to vary the resistance to simulate different riding conditions such as hill climbing.

Many participants seek out instructor-led classes for the encouragement and expertise that an instructor may provide during the exercise program, or the camraderie between participants. However, instructor-led classes generally adhere to a predetermined time schedule. This presents a problem to participants that cannot attend predetermined classes because of their jobs or other scheduling conflicts.

Health clubs typically have different types of stationary exercise bikes available on their floors for individuals to ride. However, these bikes typically do not have the open geometry, adjustability or other characteristics that allow an individual to experience an exercise program such as provided by indoor cycling programs. In other words, the bikes themselves are inadequate.

Certain health clubs may have indoor cycling bikes available on their floor to ride by individuals who are not participating in an instructor-led class. But without an instructor, the individual may not receive the proper instruction or guidance essential to simulating the different riding positions and/or resistances and/or pedal cadences that an instructor typically provides during a class. Indeed, instructors such as certified SPINNING® instructors receive significant and ongoing training in order to lead classes. Accordingly, the individual that simply pedals a stationary exercise bike on a health club floor will generally not achieve the benefits of an instructor-led class. Furthermore, the lack of an instructor may increase the danger of injury if the individual is not riding the bike correctly. This may be especially so where the bike is in a direct drive or fixed gear configuration.

Accordingly, a need exists for a stationary exercise bike for use by an individual who is not participating in an instructor-led class, wherein the bike itself allows different riding positions and conditions, and also provides instruction to the individual so that the individual may receive benefits typically received during an instructor-led class. There also exists a need for the stationary bike to take the rider's ability, past exercise history and/or heart rate into account.

Previously, videos of an instructor providing instruction for an indoor cycling bike class have been available for an individual to watch as he or she rides an indoor cycling bike. However, such videos require a separate VCR and monitor to play the video. Besides requiring additional equipment, the space required may also not be available. For example, space on a health club floor is generally considered to be at a premium.

U.S. Pat. No. 6,287,239 to Hernandez purports to disclose the use of an indoor cycling bike and a display screen with a cartridge that plays music and provides directions to the rider. However, the disclosure of the '239 patent is very limited and the bike pictured in the patent would not enable a participant to simulate different riding positions and conditions, or experience an indoor exercise bike program. The '239 patent also does not disclose how the rider's ability, past exercise history and/or heart rate may be taken into account when providing instructions to the participant.

The present invention solves the above-identified needs.

SUMMARY OF THE INVENTION

In a first aspect of the invention, a stationary exercise bike for Indoor cycling is used along with a display that provides instruction to lead a rider through an exercise ride.

In another aspect of the invention, a stationary exercise bike that takes into account the rider's ability, cadence, distance, time, past exercise history and/or heart rate is described.

In another aspect of the invention, a method of exercising with the foregoing bike and display is described.

DETAILED DESCRIPTION OF THE PREFERRED EMBODIMENTS

Generally, the invention serves to provide instructions to a rider that leads the rider through an exercise program. It is preferred that the instruction be similar to that provided in instructor-led classes so that the rider obtains the benefits of such classes despite the fact that the rider's schedule conflicts with pre-scheduled instructor-led classes.

Figure 1:
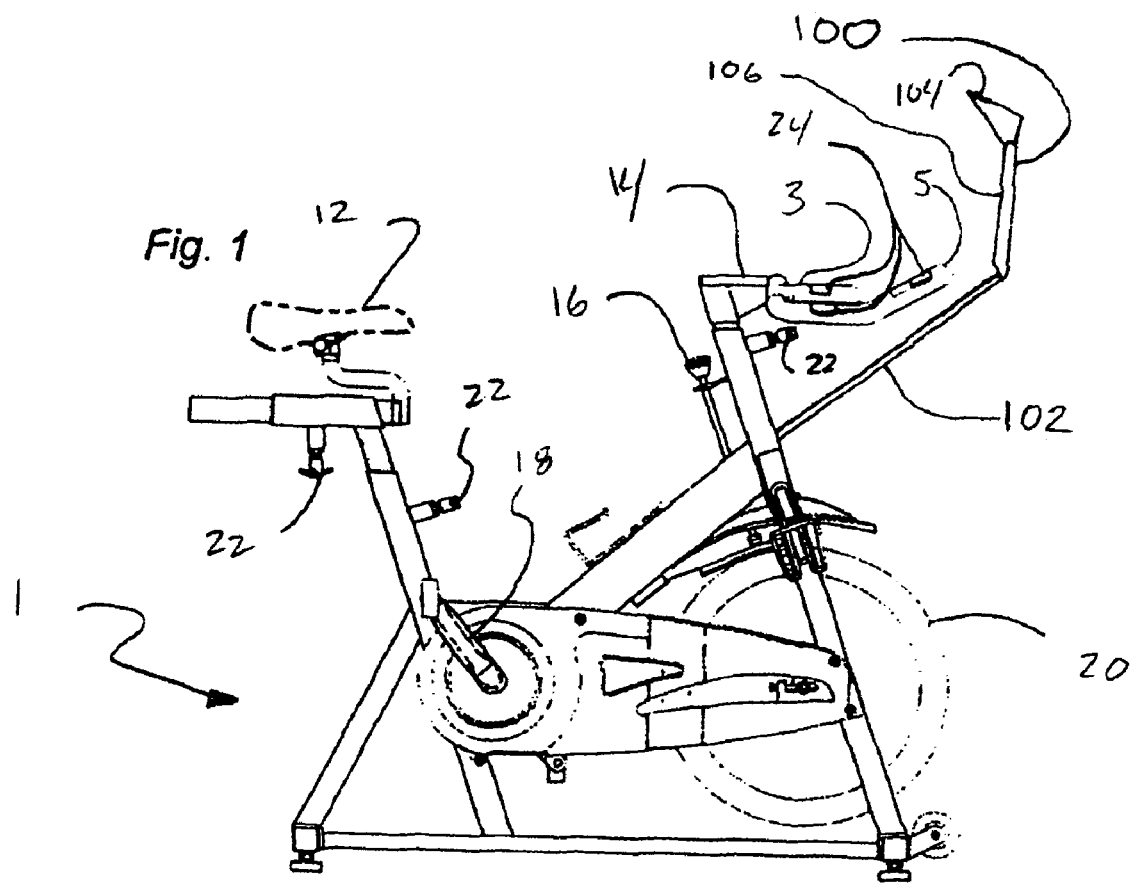
FIG. 1 shows a stationary exercise bike with a display screen.

FIG. 1 shows a stationary exercise bike 10 along with a display screen 100. The display screen includes a computer or other device to store and/or provide instructions. The bike 10 shown is an indoor cycling bike that is adjustable and has an open geometry that allows a rider to simulate different riding positions and conditions. Bike 10 preferably includes adjustable seat assembly 12, adjustable handlebar 14 having multiple hand position, variable resistance mechanism 16, pedal assembly 18 and flywheel 20 which is coupled to pedal assembly 18 in a direct drive (fixed gear) and/or non direct drive e.g., freewheeling configuration. U.S. Pat. Nos. 6,468,185 and 6,793,608 are hereby incorporated by reference herein. A clutching mechanism may also be included which may be preferred where bike 10 is in a fixed gear configuration. U.S. Pat. No. 5,961,424 is hereby incorporated by reference herein.

Various pop-pins (or other suitable mechanism) 22 may be used to effect up/down and fore/aft adjustment of seat 12, and up/down adjustment of handlebar 14. It is preferred that the seat and handlebar be adjusted to safely accommodate different riding positions such as sitting and standing, as well as different hand positions. Handlebar 14 may include one or more sensors 24 to measure the rider's pulse and heart rate. This information may be sent to the computer (discussed below). The computer may also receive heart rate signals from a montior/transmittor worn by the rider.

Display 100 may be attached to bike 10 by a bracket 102. Display 100 includes screen 106 on which various information is input and/or displayed. Brackets different than that shown may be used, and bracket 102 may attach to bike 10 at different locations. It is preferred that display 100 not interfere with the rider's ability to grasp handlebar 3 at different locations so that the rider may assume different riding positions. For example, when the rider is standing and his or her hands are near the forward end 5 of handlebar 3, it is preferred that display 100 not interfere with this position. It is also preferred that display 100 be located so that the rider does not excessively sweat on it. The display 100 preferably comprises an outer shell of plastic or other material that is resistant to sweat.

Display 100 may also be fitted with a hood 104 that may extend around the top of display 100 to provide better contrast between the ambient light and the information illuminated on display 100. Hood 104 may also extend around the sides and bottom of display. Hood 104 may also help prevent excessive sweat from dripping on display 100. Screen 106 may comprise a computer screen, LED or other type of visual display. Screen 106 may receive and/or display numerical, textual, or graphical information.

Figure 2A:
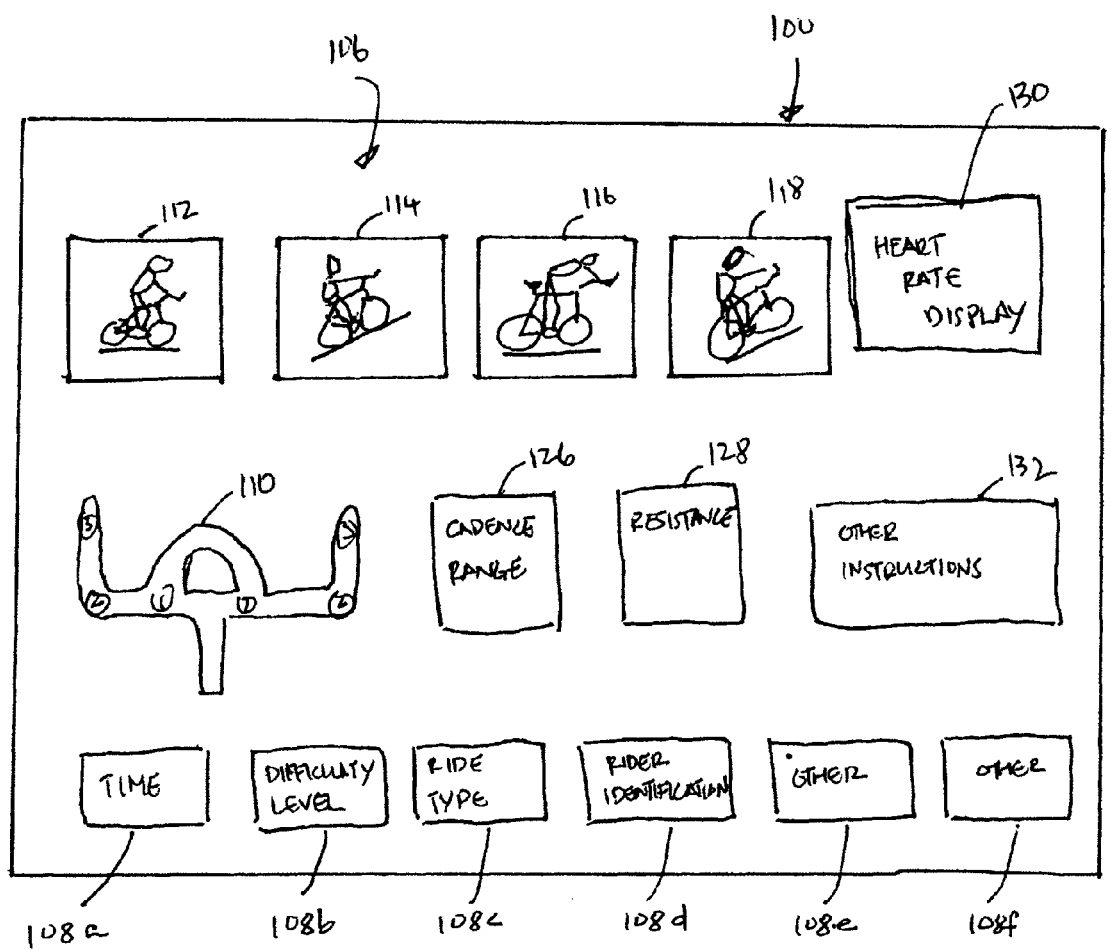
FIG. 2A shows a front view of a display featuring the display screen.
Figure 2B:
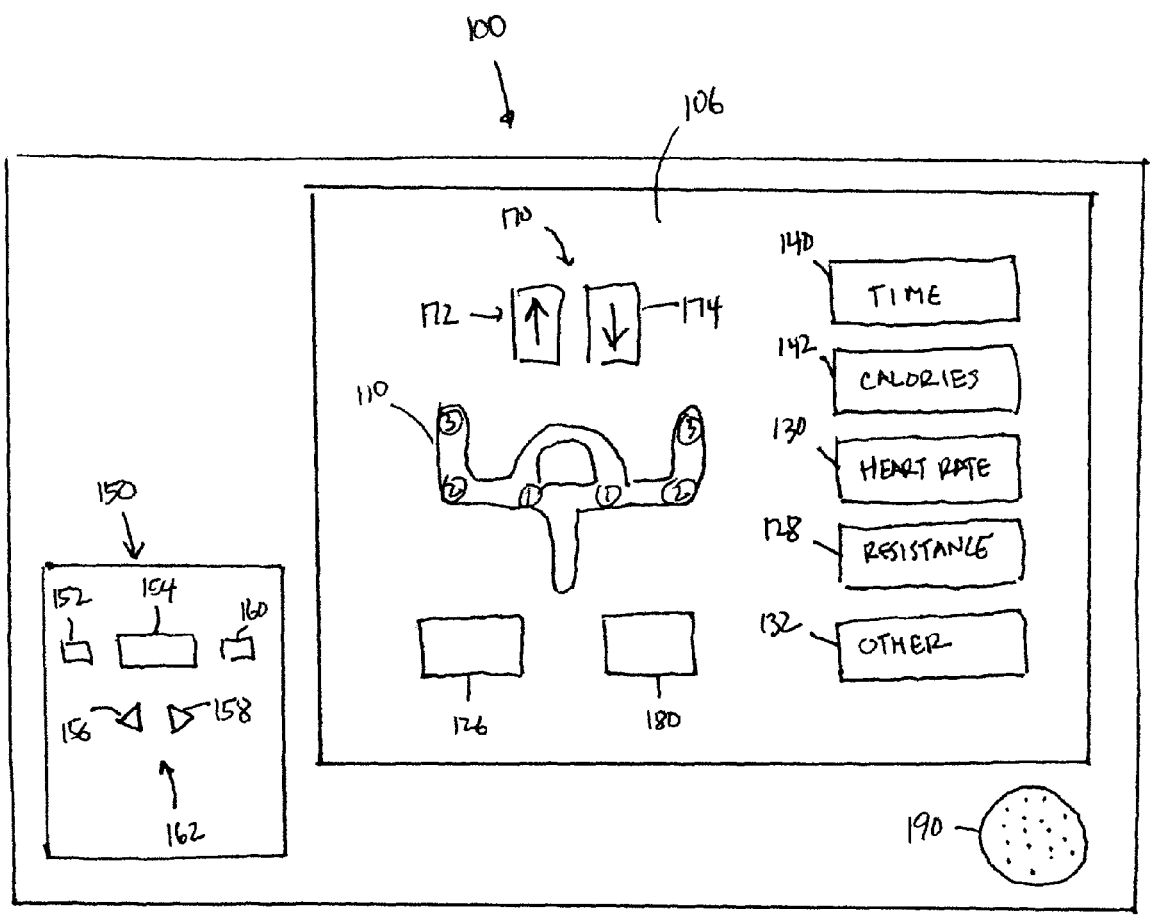
FIG. 2B shows an alternate front view of a display.
Figure 3:
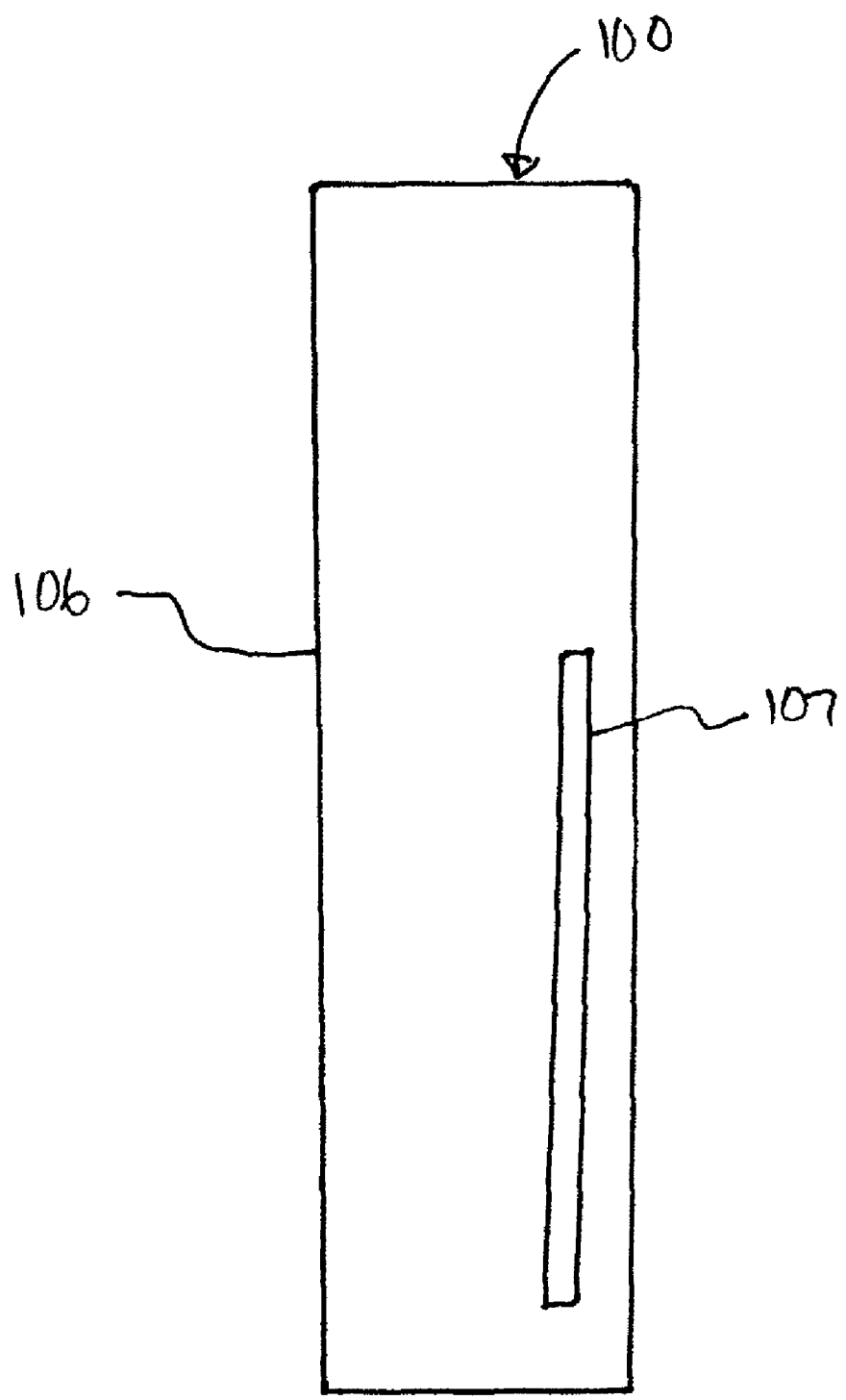
FIG. 3 shows a side view of a display.

Display 100 is now further discussed with reference to FIGS. 2A, 2B, and 3. It should be noted that the exact visual components displayed on screen 106 of the display 100 may vary from that shown in FIG. 2A or 2B or be a combination thereof. A computer or other storage device (not shown) is preferably contained within display 100. However, the computer or other storage device may be remotely located. The computer preferably stores riding instructions that are conveyed to the rider through display 100. The computer may also receive instructions and/or data from the rider through an input device 150 contained within the display 100 so that the instructions provided during the ride may be customized per the rider's specifications.

The input device 150 may be accessed through a menu button 152 and viewed through the menu screen 154. Each time the menu button 152 is pressed, one of a plurality of parameters is accessed. Once a particular parameter is accessed, a pair of directional arrows 162 may be used to scroll through the various possibilities. The left arrow 156 generally changes the value lower while the right arrow 158 generally changes the value higher. The rider may then select a particular value or parameter by pushing the select button 160.

The following is a list of the various parameters which may be accessed and set through input device 150, but is not intended to be exhaustive.

Time duration for the workout. Generally, a default time for the workout may be set. However, the rider may choose to shorten or lengthen the workout time as they desire. Once the workout starts, the overall time and/or time remaining may be displayed on the time display 140 that is located in the display screen 106.

The calories to be burned during the workout. The number of calories the rider wishes to burn may be selected by the rider. As the workout begins, the number of calories burned may be displayed on the calorie display 142 that is located in the display screen 106.

Level of intensity. Rather than selecting the number of calories burned, the rider may choose to simply select an intensity level and allow the computer to generate an appropriate workout routine. The higher the level of intensity chosen, the computer may generate a workout with greater resistance, a higher level of cadence, and/or instruct the rider to assume riding positions that are generally considered more difficult.

Type of ride, e.g., hill, flat, random or other types of pre-programmed workout. Depending on the type of workout, the display 100 may provide different types of instructions. For example, a hill ride might involve more sitting than standing.

Weight of the rider. The rider may enter this information to determine the effect on calories burned or other parameters.

Maximum heart rate. A maximum heart rate may be calculated using age-predicted charts, e.g., by subtracting the rider's age from 220 for male riders and subtracting from 226 for female riders. A more accurate rate may be determined by undergoing a maximum heart rate test. The maximum heart rate preferably enables the computer to control the workout by decreasing or increasing the level of intensity to achieve a desired heart rate level.

Identification Number. The rider may be assigned to an identification number, thereby allowing the computer to access and store certain information about a particular rider. Once assigned to a particular identification number, the rider may log in with the identification number to identify themselves and store various workouts in the computer. The computer may store the workout parameters and rider's fitness progress based on the duration of the workout, power exerted during prior workouts, calories burned or other parameters.

In this manner, the computer may automatically devise a set of instructions that push the rider to achieve a new fitness level by generating progressively more difficult workout routines. The computer may also have safeguards to prevent the rider from being advanced to quickly. For example, the computer may generate more difficult workouts only after a particular rider has had at least some number of workouts during a certain time period. The rider may also save workout routines under their identification number for easy access in the future.

As an alternative to the computer discussed above, display 100 may include a device to receive a CD-ROM, DVD, VHS tape or other storage medium that contains or receives riding instructions. As shown in FIG. 3, display 100 may include opening 107 to receive such a storage media.

Alternatively, display 100 may include a device enabling connection of the computer with the internet or some other computer network. In this embodiment, the computer may send and receive data over the internet.

The inputting of information is now more specifically described. By way of example, the first time a rider presses the menu button 152, the menu screen 154 may flash "ID" or some other appropriate message to indicate the rider should input their identification number. The directional arrows 162 may be used to scroll through the various possibilities from "None" to a numerical value ranging from 1 to however many unique users may be supported by the computer's memory. It is noted that today's storage media have large memory capacities providing for the storage of information for many riders. Alternatively, the rider may punch in his or her ID number. The computer may also request a password be entered. It is also contemplated that other forms of identification may be used such as a Smart Card, memory key, or other similar device.

If "none" is selected using the select button 160, the menu screen may ask the rider if they would like to be assigned to an identification number. The rider may select the next available number and provide password information. The rider can then move through and select a value for each of the parameters discussed above in a similar fashion.

At the end of each workout routine, if the workout was assigned to an identification number, the menu screen 154 may ask the rider if they wish to record the workout as part of their history file. Then, if the workout routine was a new routine that was not previously saved, the menu screen 154 will ask the user if they wish to save the workout routine. If the answer is yes, then the rider may name the workout routine.

Once again, the directional arrows 162 and the select button 160 may be used to scroll through and select letters and numbers to name the workout routine. In this manner ride profiles may be stored in the computer so that they may be recalled at a later time. For example, when the rider comes to the rider identification screen, a separate instructions display 132 that is located in the display screen 106 may list the ride profiles previously stored by the rider and ask the rider to choose one.

The computer may store and generate any number of work out routines including pre-programmed ones, routines saved by the user, and new routines based upon the rider's specific parameters.

Screen 106 preferably includes icons and screens that instruct the rider through the workout with different hand positions, riding positions, and varying pedaling speeds. Hand positions are shown to the rider with a handlebar icon 110 which may include first, second and third hand positions (110(1), 110(2) and 110(3)) that light up at different times signifying that the rider should change his or her hand positions. Hand positions 110(1), 110(2) and 110(3) preferably illuminate at appropriate times.

The rider's appropriate position may be shown to the rider through a pair of arrow icons 170 comprised of an up arrow icon 172 and a down arrow icon 174. When the workout requires the rider to be in the standing position, the up arrow icon 172 may be illuminated. When the workout requires the rider to be in the sitting position, the down arrow icon 174 may be illuminated. Both the up arrow icon 172 and the down arrow icon 174 may be illuminated when the rider is to alternate between standing and sitting.

Screen 106 may also include a target cadence display 180 that provides the rider with a certain range of desired cadence. The cadence range displayed may change as the riding position change. For example, a higher cadence range may be specified when the rider is seated and a lower cadence range may be specified when the rider is standing and climbing.

The computer in display 100 may be coupled to the pedal assembly 18 so that the computer may measure the rider's actual cadence. If the rider's cadence is within the desired range being displayed on a target cadence display 180 located in the display screen 106, a cadence screen 126 that is also located on the display screen 106 may illuminate in a certain way, e.g., non-flashing. If the rider's cadence is not within the desired range shown on the target cadence display 180, the rider's cadence screen showing the rider's actual cadence may illuminate in a flashing manner which preferably attracts the rider's attention so that the rider may adjust his or her cadence to bring it within the desired range.

Alternatively, screen 106 preferably includes a series of icons that instruct the rider through the ride with different combination of hand positions, riding positions, e.g., sitting or standing, and different riding conditions, e.g., flats, hills, climbing, sprinting, etc. The icons may be associated with a particular type of indoor cycling, or may be self-explanatory.

For example as shown in FIG. 2, the icons may comprise a graphic that illustrates a rider on a bike. Riding position icons may include seated flat 112, seated climbing 114, standing flat 116, and standing climbing 118. Each of these riding positions icons may light up at different times throughout the ride to signify that the rider should change positions. In this manner, the rider need not memorize riding position symbols that may be associated with a particular type of indoor cycling. As another alternative, or in addition to the foregoing, word text, such as "sit" or "stand", may illuminate on screen 106 to help instruct the rider's position.

Screen 106 may also include a resistance display 128 that provides the rider with an instructed resistance level. The resistance displayed may vary when different riding position icons are illuminated. For example, the resistance may be increased when the standing climbing icon 118 is illuminated. (Generally, in this situation, hand position 3 (110(3)) will be illuminated.) The rider may adjust the resistance device according to the resistance displayed. When the resistance value on display 128 changes, it may flash to attract the rider's attention so that the rider may change the resistance at the appropriate time. Alternatively, the resistance may be computer controlled and change automatically.

The cadence may be increased while the resistance remains constant to effect cadence building. The resistance may be increased while the cadence remains constant to effect resistance loading. The foregoing may be achieved by varying the numbers displayed on the target cadence display 180 and/or the resistance display 128.

Screen 106 also preferably includes a heart rate display 130 which displays the rider's heart rate as picked up by the sensors 24 on the handlebar 14 or monitor/transmitter worn by the rider. The location of sensors 24 in handlebar 14 preferably correspond to hand positions 1, 2 and 3 on handlebar icon 110. The heart rate may affect the instructions provided to the rider. For instance, if too high of a heart rate is recorded for too long, the rider may be instructed to slow the pedaling cadence through the target cadence display 180 and/or to assume a different riding position that requires less exertion.

Additionally, the sensors 24 may be coupled with lights that turn on to signal to the rider the appropriate position for the rider's hand.

In addition the display 100 may also include a speaker 190. The speaker may be connected to a computer, a stereo, a video monitor, or other type of multi media device. The speaker 190 may be used to enable riders to hear audible beeps indicating a change is position is needed. The speaker 190 may also enable the rider to listen to instructions or information as well as various entertainment media such as music.

Bike 10 of the current invention provides many benefits over other stationary bikes that may include some amount of computer guidance. Many such stationary bikes simply do not offer the type of workout that the current bike offers. For example, the LIFECYCLE type bike does not have the geometry to permit alternating standing and sitting in a smooth manner. In contrast, bike 10 of the current invention is intended for alternating standing and sitting and thus allows different riding positions. This in turn burns more calories and provides for a total body workout by using different muscle groups. For example, the standing position allows core abdominal muscles to be used. This is not achieved by the LIFECYCLE type bike.

The LIFECYCLE type bike does not provide instructions regarding various riding and handlebar positions that allow for a workout that involves a bike ride that simulates an outdoor ride with flats, hills and other conditions. Bike 10 of the current invention provides these type of instructions. The LIFECYCLE type bike also does not offer the variety of personalized rides that bike 10 of the current invention offers.

The current invention also provides an advance over indoor cycling bikes that may be located on the health club floor for random use without an instructor. These other type of indoor cycling bikes may pose a safety threat, especially when in a fixed gear configuration. Bike 10 of the current invention may provide instructions regarding a cadence limit, or other variables to reduce or avoid this risk. The instructions may also take the rider's health into account. Accordingly, bike 10 overcomes some of the risks associated with random, non-instructed use of indoor cycling bikes that are typically used in a group class led by an instructor.

Although certain presently preferred embodiments of the invention have been described herein, it will be apparent to those skilled in the art to which the invention pertains that variations and modifications of the described embodiments may be made without departing from the spirit and scope of the invention.

I claim:

1. An exercise device, comprising:
   a stationary bike having a resistance adjustment mechanism for a rider to adjust the pedaling resistance of the stationary bike;
   a computer coupled to the stationary bike, the computer containing instructions for a customized ride created by a rider based on the rider's specifications;
   a display coupled to the computer, wherein the display conveys instructions to the rider based on the rider's specifications, the instructions including varying hand positions on a handlebar; varying riding positions including alternating sitting and standing positions; varying cadence ranges that are varied as the riding positions vary; and varying the resistance adjustment mechanism and/or cadence based on the rider's heart rate; and
   an input device coupled to the display, wherein the input device enables the rider to input data into the computer to customize the ride per the rider's specifications.

2. The exercise device of claim 1, wherein the input device further comprising:
   a menu button;
   a menu screen accessed by the menu button;
   a pair of directional arrows to scroll through the data on the menu screen; and
   a select button to choose a selection from the menu screen.

3. The exercise device of claim 1, wherein the display includes a handlebar icon, the handlebar icon providing instructions to the rider on where to place the hands.

4. The exercise device of claim 3, wherein the handlebar icon includes a first, a second, and a third hand position that lights up to indicate the location of the rider's hand position.

5. The exercise device of claim 1, wherein the display includes a pair of arrow icons comprising an up arrow icon and a down arrow icon.

6. The exercise device of claim 5, wherein the up arrow icon is illuminated to indicate the rider should stand, the down arrow icon is illuminated to indicate that the rider should sit, and both the up arrow icon and the down arrow icon are illuminated to indicate the rider should get into a jumping motion.

7. The exercise device of claim 1, wherein the display includes a target cadence display, the target cadence display revealing the appropriate cadence at which the rider should be pedaling.

8. The exercise device of claim 1, wherein the display includes a cadence screen, the cadence screen indicating the rider's actual cadence.

9. The exercise device of claim 8, wherein the cadence screen flashes to inform the rider to either pedal faster or slower and stays constant without flashing to indicate the rider should maintain the current cadence.

10. The exercise device of claim 1, wherein the computer provides instructions to the rider to adjust the resistance adjustment mechanism to fluctuate levels of resistance to imitate cycling situations encountered on the road.

11. The exercise device of claim 1, wherein the display is surrounded by an outer shell composed of a water resistant material.

12. The exercise device of claim 1, wherein the display is protected by an opaque hood attached to the display along its outer perimeter.

13. The exercise device of claim 1, wherein the computer contains a number of preprogrammed workout routines.

14. The exercise device of claim 1, wherein the computer stores additional workout routines designed by the rider.

15. The exercise device of claim 1, wherein the computer retains at least one rider's workout history by keeping track of the rider's workout frequency and intensity level of the rider's workout.

16. The exercise device of claim 1, wherein the computer receives heart rate signals from a transistor worn by the rider and provides instructions to the rider to vary the resistance adjustment mechanism and/or cadence based on the heart rate signals.

17. The exercise device of claim 1, wherein the computer receives heart rate signals from a sensor located on the handlebar and provides instructions to the rider to vary the resistance adjustment mechanism and/or cadence based on the heart rate signals.

18. The exercise device of claim 17, wherein the sensor is coupled with a light that lights up to indicate the appropriate location for the rider's hands.

19. The exercise device of claim 1, wherein the computer generates a riding program based upon a rider's weight, a total workout time, and a desired number of calories the rider wishes to burn during the workout routine.

20. The exercise device of claim 1, wherein the computer generates a riding program based upon a rider's weight, a difficulty level selected by the rider, and a total workout time.

21. The exercise device of claim 1, wherein the display shows the rider's speed.

22. The device of claim 1, wherein the display shows the rider's heart rate.

23. The device of claim 1, wherein the display shows the number of calories burned by the rider.

24. The device of claim 1, wherein the display shows the time remaining or elapsed time in the workout routine.

25. The device of claim 1, wherein the display shows the resistance level.

26. The exercise device of claim 1, wherein the display is configured to receive a multi-media device.

27. The exercise device of claim 1, wherein the display includes a separate symbol for each position that the rider may perform, the symbol lighting up to instruct the rider to change into the desired position.

28. The exercise device of claim 1, wherein the computer is connected to the internet.

29. An exercise device, comprising:
   a stationary bike having a resistance adjustment mechanism for a rider to adjust the pedaling resistance of the stationary bike;
   a computer coupled to the stationary bike, the computer containing instructions on how to carry out a customized stationary bike workout routine based on the rider's specifications;
   a display coupled to the computer, wherein the display conveys instructions for a ride by a rider based on the rider's specifications, the instructions being provided through a handlebar icon, a pair of arrow icons, and a cadence screen; the instructions including varying the resistance adjustment mechanism and/or cadence based on the rider's heart rate;
   a hood attached to the display along its outer perimeter; and
   an input device for the rider to input the rider's specifications into the computer, the input device being coupled to the display, wherein the input device includes:
   a menu button;
   a menu screen accessed by the menu button;
   a pair of directional arrows to scroll through the data on the menu screen; and
   a select button to choose a selection from the menu screen.

30. An exercise device, comprising:
   a stationary bike having a resistance adjustment mechanism for a rider to adjust the pedaling resistance of the stationary bike;
   a computer coupled to the stationary bike, the computer containing hand positions, riding positions and cadence instructions for a customized ride created by a rider based on the rider's specifications;
   a display coupled to the computer, wherein the display includes a handlebar icon, a riding position icon and a cadence display, the handlebar icon providing instructions to the rider on where to place the rider's hands, the riding position icon providing instructions to the rider on the riding position to assume, including alternating sitting and standing riding positions, and the cadence display providing instructions to the rider to vary cadence according to the riding position assumed, and wherein the display provides instructions to vary the resistance adjustment mechanism and/or cadence based on the rider's heart rate; and
   an input device coupled to the display, wherein the input device enables the rider to input the rider's specifications into the computer.

* * * * *